US008053416B2

(12) United States Patent
Pettit et al.

(10) Patent No.: US 8,053,416 B2
(45) Date of Patent: Nov. 8, 2011

(54) ISOLATION AND STRUCTURE OF TURBOSTATINS 1-4

(75) Inventors: George R. Pettit, Paradise Valley, AZ (US); Yuping Tang, Tempe, AZ (US)

(73) Assignee: Arizona Board of Regents, a body corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 642 days.

(21) Appl. No.: 11/913,169

(22) PCT Filed: May 11, 2006
(Under 37 CFR 1.47)

(86) PCT No.: PCT/US2006/018382
§ 371 (c)(1),
(2), (4) Date: Oct. 8, 2008

(87) PCT Pub. No.: WO2006/122296
PCT Pub. Date: Nov. 16, 2006

(65) Prior Publication Data
US 2009/0298784 A1    Dec. 3, 2009

Related U.S. Application Data

(60) Provisional application No. 60/679,853, filed on May 11, 2005.

(51) Int. Cl.
*A61K 31/7028* (2006.01)
*C07H 15/02* (2006.01)

(52) U.S. Cl. .......................................... 514/25; 536/17.9

(58) Field of Classification Search ............. 514/25; 536/17.9
See application file for complete search history.

(56) References Cited

U.S. PATENT DOCUMENTS
5,936,076 A    8/1999   Higa et al. ................. 536/17.9

FOREIGN PATENT DOCUMENTS
WO    WO 2005/014008 A2 *   2/2005

OTHER PUBLICATIONS

International Search Report for PCT/US2006/018382 dated Aug. 30, 2006.
Written Opinion of the International Search Authority for PCT/US2006/018382 dated Aug. 30, 2006.

* cited by examiner

*Primary Examiner* — Shaojia Anna Jiang
*Assistant Examiner* — Ganapathy Krishnan
(74) *Attorney, Agent, or Firm* — McAndrews Held & Malloy Ltd.

(57) ABSTRACT

Described herein are novel cerebroside compounds, designated as Turbostatin 1, Turbostatin 2, Turbostatin 3, and Turbostatin 4. These compounds were extracted and isolated from the marine mollusk *Turbo stenogyrus*, and their structures elucidated. The new compounds exhibit significant cancer cell growth inhibition activity against a variety of murine and human cancer cell lines, and as such appear will be useful in the treatment of various forms of neoplastic disease.

13 Claims, 1 Drawing Sheet

1, n = 13
2, n = 15

3, n = 13
4, n = 15

ISOLATION AND STRUCTURE OF TURBOSTATINS 1-4

CROSS-REFERENCE TO RELATED APPLICATIONS

This application is the U.S. national stage of PCT/US2006/018382 filed on May 11, 2006, which is based on and claims the priority of U.S. Provisional Patent Application No. 60/679,853 filed on May 11, 2005, the disclosure of which is incorporated herein in its entirety by reference thereto.

STATEMENT REGARDING GOVERNMENT FUNDING

This invention was made with government support under Grant Number CA 90441-01-03 awarded by the National Institute of Health and Arizona Disease Control Research Center Contract Number 7011. The government has certain rights in the invention.

FIELD OF THE INVENTION

The present invention is directed to novel cell growth inhibitory compounds derived from a marine organism, said compounds exhibiting antineoplastic activity. The present invention is further directed to methods of inhibiting cancer cell growth and/or microbial growth in a host inflicted therewith by administering the novel compounds to the inflicted host.

BACKGROUND OF INVENTION

Topshells of the marine phylum Mollusca are members of the gastropod family Trochidae and are best known for use of some species in the manufacture of pearl ornaments and as a seafood in the Caribbean and Central America. Since topshells are primarily algae feeders, it is not surprising that one species, *Turbo pica* has been reported to contain toxic tissue (2). In 1968, one or more of the inventors found the snail component from 0.5 kg of *T. stenogyrus* to give a 2-propanol extract which displayed strong activity (T/C at 400 mg/kg) against the murine P388 lymphocytic leukemia (in vivo) (References 3,4). In 1971 they proceeded with the 2-propanol extract from 22.7 kg of *T. stenogyrus*, and with separation techniques then available, isolated taurine as one of the anticancer constituents (Ref. 4). Evaluation of taurine using P388 in vivo at dos levels from 4.0 to 800 mg/kg led to T/C values that never exceeded 123 (i.e., 23% increase in median survival time). Furthermore, taurine was found inactive against the in vivo L-1210 lymphoid leukemia and human epidermoid carcinoma of the nasopharynx (KB) cell line.

Using recent bioassay and chemical separation techniques, the inventors have isolated and elucidated the structure of four specific compounds, said compounds being cancer cell growth inhibitory glycosphingolipids. Thus, the present invention involves the discovery of pure forms of certain compounds from extracts of *T. stenogyrus*.

SUMMARY OF THE INVENTION

The present invention relates to the isolation and structural elucidation of certain glycosphingolipid compounds from a marine organism, the Asian topshell snail *Turbo stenogyrus*. The invention further relates to the use of those purified compounds as antineoplastic agents in the treatment of human and animal hosts afflicted with neoplastic disease. The compounds of the present invention have been denominated Turbostatin 1, Turbostatin 2, Turbostatin 3 and Turbostatin 4. The invention also includes salts of the foregoing novel compounds, such as pharmaceutically acceptable salts thereof.

DETAILED DESCRIPTION OF THE INVENTION

Figure 1:
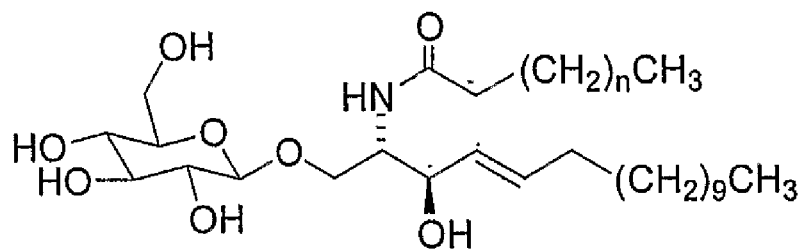
FIG. 1 illustrates the structure of Turbostatins 1 and 2.
Figure 2:
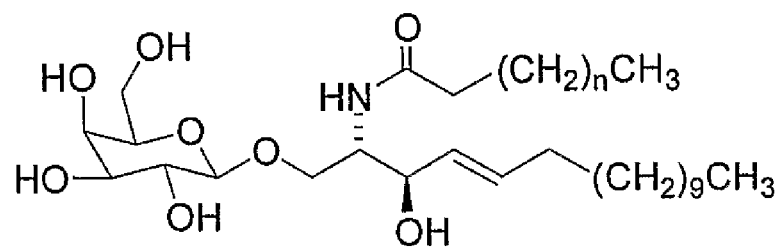
FIG. 2 illustrates the structure of Turbostatins 3 and 4.

The following describes the method used to obtain the compounds of the invention from the marine organism *T. stenogyrus*.

Results and Discussion

The evaluation of *T. stenogyrus* fractions was greatly assisted by the availability of the P388 cell line and human cancer cell lines for bioassay-directed separations, especially combined with recent advances in general separation procedures and HPLC equipment. An aliquot of the 1971 2-propanol extract of *Turbo stenogyrus* was first subjected to a 9:1→3:2 $CH_3OH$—$H_2O$/Hexane→$CH_2Cl_2$ solvent partition sequence. The final active methylene chloride extract (P-388: $ED_{50}$ 3.52 µg/mL) was carefully fractionated by an extensive series of separations involving column gel permeation (Sephadex LH-20), partition chromatography, and a final isolation by reverse-phase HPLC columns on Zorbax SB-C18 in 85:15 $CH_3OH$—$H_2O$. These procedures afforded colorless glycosphingolipids 1-4, which the inventors denominated Turbostatins 1-4, as amorphous solids.

Turbostatin 1

The turbostatin 1 (1) molecular formula was assigned $C_{38}H_{74}NO_8$ on the basis of high-resolution APCI mass ([M+H]$^+$ at m/z 672.53192), $^1$H- and $^{13}$C-NMR spectral analyses (Table 1). An IR absorption band at 3393 cm$^{-1}$ indicated the presence of hydroxyl groups. The typical IR absorptions at 1630 and 1537 cm$^{-1}$ suggested an amide linkage, which was confirmed by a nitrogen-attached carbon signal at δ 55.05 and a carbonyl signal at δ 173.32 in the $^{13}$C-NMR spectrum. The $^1$H-NMR spectrum exhibited a doublet at δ 8.35 (J=7.5 Hz) due to an NH proton, which was exchangeable with $D_2O$; a broad singlet at δ 1.21 (methylene protons); a triplet at δ 0.85 (two terminal methyls); an anomeric proton at δ 4.96 (J=8.2 Hz), and carbinol protons appearing as multiplets between δ 3.90-4.82, suggesting a glycosphingolipid structure (Ref. 8-11). The $^1$H-NMR spectrum also showed two olefinic proton signals at δ 5.97 ($^1$H, dd, J=15.0, 6.0 Hz, H-4), and 5.83 ($^1$H, dt, J=15.2, 6.0 Hz, H-5), attributable to the presence of one disubstituted double bond. The amino alcohol fragment was identified as a sphingosine unit by the characteristic signals that appeared in the $^1$H- and $^{13}$C-NMR spectra, especially owing to the presence of a typical Δ$^4$ double bond. The large vicinal coupling constants of H-4 and H-5 (J=15.0 Hz) clearly indicated an E-geometry for the double bond (Ref. 9, 10).

In the $^{13}$C-NMR spectrum the carbon resonances appeared at δ 62.74 ($CH_2$), 71.64 (CH), 75.15 (CH), 78.47 (CH), 78.48 (CH), and 105.46 (CH) revealing the presence of a β-glucopyranoside. The anomeric proton at δ 4.96 (d, J=8.2 Hz) correlated to the carbon signal at δ 105.46 in the HMQC spectrum, further confirming the β-configuration of the glucoside unit. The length of the lipid (sphingoid base) base and the lipid amide were determined by APCI-MS. In addition to the quasimolecular ion at m/z 672 [M+H]$^+$, the APCI spectrum of turbostatin 1 exhibited an intense fragment peak at m/z 510 which was produced by elimination of the glucosyl unit from the protonated molecular ion. The loss of palmitoylamide from the molecular ion gave rise to the fragment at m/z 254. The typical fragment ion at m/z 384 was formed by elimination of decene from that at m/z 510 through McLafferty rearrangement (Ref. 13, 14). Therefore, the number of carbons in the lipid base and lipid amide were both determined to be 16.

The linkages of the three component units of turbostatin 1 were deduced from the HMBC spectrum. The carbon signal at δ 173.32 (C-1') correlated with the proton signals at δ 4.81 (H-2) and 2.41 (H-2'). The proton signal at δ 4.81 (H-2) gave crosspeaks with the carbon signal at δ 72.58 (C-3) and 70.46 (C-1). In addition, the latter also correlated with the proton signal at δ 4.96 (C1"). The carbon signal at δ 72.58 (C-3) showed crosspeaks with the proton signals at δ 5.98 (H-4) and 5.85 (H-5). From these analyses, the structure of turbostatin 1 was elaborated and the overall assignments (Table 1) of $^1$H-NMR and $^{13}$C-NMR data were unambiguously made based on the $^1$H-$^1$H COSY, TOCSY, HMQC, and HMBC spectra. By considering biogenetic relationships (Ref. 15) steric factors and the chemical shift of H-2, the chemical shifts of the carbon signals of C-1 to C-3 and C-1' may be utilized to determine the absolute stereochemistry of glucosphingolipids and sphingolipids (Ref. 16-18). The proton signal at δ 4.81 (H-2) and the carbon signals at δ 70.46 (C-1), 55.05 (C-2), 72.58 (C-3), and 173.32 (C-1') of turbostatin 1 were in good agreement with those reported for glycosphingonines (as model structures) with the 2S,3R configuration. The optical rotation of turbostatin 1 ($[\alpha]^{23}_D$+10.2°) was very close to that of 1-0-(β-D-glucopyranosyl)-D-(+)-(2S,3R)-2-(docosanoylamide)-1,3-eicosanediol ($[\alpha]^{27}_D$+8.6) (Ref. 8). All of these considerations were used to assign turbostatin 1 as 1-O-β-D-glucopyranosyl-2S-hexadecanoylamino-3R-hydroxy-4E-hexadecene.

Turbostatin 2

As with turbostatin 1, the molecular formula of turbostatin 2 (2) was assigned $C_{40}H_{78}NO_8$ on the basis of high-resolution APCI mass spectroscopy ([M+H]$^+$ at m/z 700.57498) and the results of $^1$H- and $^{13}$C-NMR spectral interpretations (Table 1). The NMR results were found to be essentially identical to those of amide 1, which confirmed that turbostatin 2 (2) was also a glycosphingolipid and differed only in the length of the lipid base and lipid amide units. In addition to the quasimolecular ion at m/z 700 [M+H]$^+$, the APCI spectrum of ceramide 2 exhibited an intense fragment peak at m/z 538 which was produced by elimination of the glucosyl unit from the protonated molecular ion. The loss of octadecoylamide from the molecular ion gave rise to the fragment at m/z 254. The typical fragment ion at m/z 412 was formed by elimination of decene through McLafferty rearrangement (Ref. 13, 14) Therefore, the number of carbons in the lipid base and lipid amide were determined to be 16 and 18, respectively. Thus, turbostatin 2 was assigned structure 2.

TABLE 1

$^1$H- and $^{13}$C-NMR Spectral Assignments (δ/ppm) for Turbostatins 1 and 2 in Py-d$_5$.

| | $\delta_H$ | | $\delta_C$ | |
|---|---|---|---|---|
| Position | 1 | 2 | 1 | 2 |
| Lipid Base Unit | | | | |
| 1a | 4.82 (m) | 4.82 (m) | 70.46 | 70.42 |
| 1b | 4.23 (m) | 4.22 (m) | | |
| 2 | 4.81 (m) | 4.80 (m) | 55.05 | 55.02 |

TABLE 1-continued $^1$H- and $^{13}$C-NMR Spectral Assignments (δ/ppm) for Turbostatins 1 and 2 in Py-d$_5$.

| | $\delta_H$ | | $\delta_C$ | |
|---|---|---|---|---|
| Position | 1 | 2 | 1 | 2 |
| 3 | 4.75 (m) | 4.75 (m) | 72.58 | 72.57 |
| 4 | 5.98 (dd, 6.0, 15.0) | 5.97 (dd, 6.0, 15.2) | 132.20 | 132.21 |
| 5 | 5.85 (dt, 6.0, 15.0) | 5.83 (dt, 6.0, 15.2) | 132.51 | 132.49 |
| 6 | 2.03 (q, 7.0) | 2.01 (q, 7.1) | 32.71 | 32.71 |
| 7~15 | 1.21 (brs) | 1.21 (brs) | 22.9~32.1 | 22.9~32.1 |
| 16 | 0.85 (t, 8.6) | 0.85 (t, 8.6) | 14.25 | 14.24 |
| NH | 8.35 (d, 7.5) | 8.37 (d, 7.8) | | |
| N-Acyl Unit | | | | |
| 1' | | | 173.32 | 173.30 |
| 2' | 2.41 (t, 7.0) | 2.41 (t, 7.0) | 32.71 | 32.70 |
| 3' | 1.80 (m) | 1.80 (m) | 26.37 | 26.39 |
| 4'~15' or 4'~17' | 1.21 (brs) | 1.21 (brs) | 22.9~32.1 | 22.9~32.1 |
| 16' or 18' | 0.85 (t, 8.6) | 0.85 (t, 8.6) | 14.25 | 14.24 |
| Glycoside | | | | |
| 1" | 4.96 (d, 8.2) | 4.96 (d, 8.1) | 105.46 | 105.44 |
| 2" | 4.06 (dd, 8.4, 9.6) | 4.04 (dd, 8.1, 9.3) | 75.15 | 75.15 |
| 3" | 4.24 (m) | 4.24 (m) | 78.48 | 78.48 |
| 4" | 4.37 (m) | 4.37 (m) | 71.64 | 71.63 |
| 5" | 3.90 (m) | 3.91 (m) | 78.47 | 78.46 |
| 6a" | 4.51 (dd, 5.1, 11.7) | 4.50 (dd, 5.0, 11.6) | | |
| 6b" | 4.20 (dd, 2.3, 11.7) | 4.22 (dd, 2.3, 11.6) | 62.74 | 62.74 |

Turbostatin 3

The molecular formula of turbostatin 3 (3) was found to be $C_{38}H_{74}NO_8$ on the basis of high-resolution APCI mass spectroscopy ([M+H]$^+$ at m/z 672.54142) as well as $^1$H- and $^{13}$C-NMR spectral results (Table 2). Again, the $^1$H- and $^{13}$C-NMR spectra were found to be nearly identical to those of turbostatins 1 and 2 except for the glycoside signals and confirmed that turbostatin 3 (3) was also a glycosphingolipid. In the $^{13}$C-NMR spectrum the glycoside unit carbon resonances appeared at δ 62.34 (CH$_2$), 70.21 (CH), 72.71 (CH), 75.38 (CH), 77.07 (CH), and 106.47 (CH) revealing the presence of a β-galactopyranoside (Ref. 12). The anomeric proton at δ 4.89 (d, J=7.5 Hz) correlated to the carbon signal at δ 106.47 in the HMQC spectrum, further confirming the β-configuration of the galactose unit. The APCI-MS spectrum of cerebroside 3 also exhibited three fragment peaks at m/z 510, 384 and 254, which suggested the number of carbons in the lipid base and lipid amide were both 16. Therefore, structure 3 was determined to represent turbostatin 3.

Turbostatin 4

The molecular formula of turbostatin 4 (4) was assigned $C_{40}H_{78}NO_8$ based on the spectral data sequence: [M+H]$^+$ at m/z 700.58320 and as recorded in Table 2 which were found to be essentially identical with that of turbostatin 3 differing only in the length of the lipid base and lipid amide. The APCI-MS spectrum of amide 4 also exhibited three fragment peaks at m/z 538, 412 and 254 as already found for amide 2. This indicated the number of carbons in the lipid base and lipid amide were also 16 and 18, respectively, and allowed assignment of structure 4 to turbostatin 4.

TABLE 2

$^1$H- and $^{13}$C-NMR Spectral Assignments (δ/ppm) for Turbostatins 3 and 4 in Py-$d_5$.

| Position | $δ_H$ 3 | $δ_H$ 4 | $δ_C$ 3 | $δ_C$ 4 |
|---|---|---|---|---|
| Lipid Base Unit | | | | |
| 1a | 4.81 (m) | 4.82 (m) | 70.44 | 70.45 |
| 1b | 4.24 (m) | 4.23 (m) | | |
| 2 | 4.80 (m) | 4.81 (m) | 55.04 | 55.03 |
| 3 | 4.75 (m) | 4.75 (m) | 72.60 | 72.59 |
| 4 | 5.99 (dd, 6.0, 15.2) | 5.98 (dd, 6.0, 15.0) | 132.15 | 132.18 |
| 5 | 5.85 (dt, 6.0, 15.2) | 5.83 (dt, 6.0, 15.0) | 132.50 | 132.49 |
| 6 | 2.03 (q, 7.2) | 2.01 (q, 7.0) | 32.72 | 32.70 |
| 7~15 | 1.21 (brs) | 1.21 (brs) | 22.9~32.1 | 22.9~32.1 |
| 16 | 0.85 (t, 8.6) | 0.85 (t, 8.6) | 14.26 | 14.25 |
| NH | 8.37 (d, 7.7) | 8.36 (d, 7.8) | | |
| N-Acyl Unit | | | | |
| 1' | | | 173.33 | 173.33 |
| 2' | 2.41 (t, 7.2) | 2.41 (t, 7.1) | 32.71 | 32.70 |
| 3' | 1.80 (m) | 1.80 (m) | 26.38 | 26.38 |
| 4'~15' or 17' | 1.21 (brs) | 1.21 (brs) | 22.9~32.1 | 22.9~32.1 |
| 16' or 18' | 0.85 (t, 8.6) | 0.85 (t, 8.6) | 14.26 | 14.25 |
| Glycoside | | | | |
| 1" | 4.89 (d, 7.5) | 4.88 (d, 7.3) | 106.47 | 106.46 |
| 2" | 4.52 (dd, 7.5, 9.5) | 4.52 (dd, 7.5, 9.4) | 72.71 | 72.71 |
| 3" | 4.16 (dd, 3.0, 9.5) | 4.14 (dd, 3.0, 9.4) | 75.38 | 75.40 |
| 4" | 4.56 (d, 3.0) | 4.55 (3.0) | 70.21 | 70.22 |
| 5" | 4.07 (dd, 6.0, 9.0) | 3.07 (dd, 6.2, 8.9) | 77.07 | 77.06 |
| 6" | 4.44 (m) | 4.44 (m) | 62.34 | 62.35 |

Evaluation of Antineoplastic Activity

The compounds of the invention, Turbostatins 1-4, were evaluated against the murine P388 lymphocytic leukemia cell line and a minipanel of human cancer cell lines and were found to exhibit significant cancer cell growth inhibition against each cell line. The results of this in vitro testing is shown in Table 3.

TABLE 3

Murine P388 Lymphocytic Leukemia Cell Line and Human Cancer Cell Line Inhibition Values ($GI_{50}$ expressed in μg/mL) for Turbostatins 1-4 in DMSO.

| Cancer cell line | Compound 1 | Compound 2 | Compound 3 | Compound 4 |
|---|---|---|---|---|
| P388 (lymphocytic leukemia) | 0.27 | 0.15 | 0.25 | 0.29 |
| BXPC-3 (pancreas adenocarcinoma) | 0.71 | 1.0 | 1.6 | 0.93 |
| MCF-7 (breast adenocarcinoma); | 0.44 | 0.39 | 0.48 | 0.44 |
| SF268 (CNS glioblastoma); | 0.98 | 1.9 | 1.9 | 1.5 |
| NCI-H460 (lung large cell) | 0.34 | 0.53 | 0.55 | 0.49 |
| KML20L2 (colon adenocarcinoma) | 0.35 | 0.35 | 0.48 | 0.41 |
| DU-145 (prostate carcinoma). | 1.6 | 1.7 | 2.6 | 2.6 |

That was a promising result since some ceramides (parent is an 18 carbon lipid base, 14 carbon lipid amide) and derived hexose glycosides such as glucocerebrosides (e.g., turbostatins 1 and 2) and galactocerebrosides (e.g., turbostatins 3 and 4) function as a cellular second messenger and intermediary in a variety of important cell functions such as apoptosis, cell senescence and terminal cell differentiation[20]. Ceramide is also known to stimulate mitogen-activated protein kinase[21] through binding to protein kinase c-Raf,[22] and some cerebrosides are known to possess anticancer, antiviral, antifungal, antimicrobial, Cox-2 inhibitory, immunostimulative and immunosuppressive activities. Some of these properties would appear promising for the treatment of Alzheimer's disease Interestingly, α-alactosylceramides have been shown earlier to have anticancer activity. As an illustration, KRN7000 has been shown to display remarkable activity against a disparate group of diseases, such as cancer, including melanoma, pancreatic and colon cancer, as well as malaria, juvenile diabetes, hepatitis B and autoimmune encephalomyelitis, using in vivo versions of these diseases.

Thus, it is believed that the compounds of the invention, turbostatins 1-4, may have a useful role in inhibiting the sphingolipid biochemical pathways of the cancer cell, as well as for the treatment of other diseases and conditions which implicate similar pathways.

Experimental Section

General Experimental Methods. Melting points were measured using an Olympus electrothermal melting point apparatus and are uncorrected. IR spectra were recorded with a Thermo Nicolet Avatar 360 infrared spectrometer. NMR spectra were obtained with a Varian XL-300 or a Varian UNITY INOVA-500 spectrometer with tetramethylsilane (TMS) as an internal reference. High-resolution mass spectra were obtained using a JEOL LCMate magnetic sector instrument in the APCI positive mode, with a polyethylene glycol reference.

All chromatographic solvents were redistilled. Sephadex LH-20 used for partition column chromatography was obtained from Pharmacia Fine Chemicals AB. Analytical HPLC was conducted with a Hewlett-Packard Model 1050 HPLC coupled with a Hewlett-Packard diode-array detector. Semipreparative HPLC was performed on a Waters Deltaprep-600 instrument on 9.4×250 mm columns of Zorbax SB-C18.

*Turbo stenogyrus*: The topshell *T. stenogyrus* (phylum Mollusca, class Gastropoda, subclass Prosobronchia) is a member of the Turbinidae family in the order Archaeogastropoda. A summer of 1971 recollection (22.7 kg; from along the coast of Taiwan) of *T. stenogyrus* was employed in the present study and supplied by Mr. Elliot Glanz, The Butterfly Company, Brooklyn, New York, N.Y., in 1968. The voucher specimen is maintained in our Institute, and the taxonomic authority was Dr. I. E. Wallen, Smithsonian Oceanographic Sorting Center, Smithsonian Institution, Washington, D.C., 20560.

Extraction and Initial Separation of *T. Stenogyrus*. The snail portion of the 1971 recollection *T. stenogyrus* was extracted with 2-propanol. The extract (the long period of storage was in a tightly sealed glass container, maintained in the dark at ca. 20° C.) was dissolved in $CH_3OH$—$H_2O$ (9:1) and the solution filtered to remove insoluble material. The resulting solution was partitioned four times between hexane and 9:1 $CH_3OH$—$H_2O$. The hexane layer was removed and concentrated to yield 13.3 g (P388 $ED_{50}$ 60 μg/mL) of black-brown material. The $CH_3OH$—$H_2O$ phase was diluted to give a ratio of 3:2 (by addition of $H_2O$) and extracted four times with $CH_2Cl_2$, the $CH_2Cl_2$ layer was concentrated to afford a black oily P388-active (14.7 g, $ED_{50}$ 3.52 μg/mL) fraction. The remaining $CH_3OH$—$H_2O$ solution was P388 cell line inactive.

Isolation of Turbostatins 1-4 (1-4). A 14.6-g aliquot of the P388-active $CH_2Cl_2$ fraction was partially dissolved in $CH_3OH$, and the solution was filtered and separated on a Sephadex LH-20 column with $CH_3OH$ as eluent. Ten fractions were obtained. One of the fractions (2.5 g, $ED_{50}$ 1.25 μg/mL) was further separated on a Sephadex LH-20 column in $CH_3OH$—$CH_2Cl_2$ (3:2) to yield seven fractions. A 1.4-g fraction with $ED_{50}$ 0.30 μg/mL was rechromatographed on a Sephadex LH-20 column in hexane-$CH_3OH$-2-propanol (8:1:1). Two fractions obtained from this step showed P388 activity, and a 180-mg fraction with $ED_{50}$ 0.76 μg/mL was further separated on a Sephadex LH-20 column in hexane-toluene-acetone-$CH_3OH$ (1:4:3:4). Six active fractions were combined and rechromatographed on a Sephadex LH-20 column using hexane-ethanol-toluene-$CH_2Cl_2$ (17:1:1:1) as eluent. Four active fractions were obtained, recombined and rechromatographed on a Sephadex LH-20 column with hexane-EtOAc—$CH_3OH$ (4:5:1) as eluent. All five fractions obtained from this step showed P388 activity and a 56-mg fraction with $ED_{50}$ 0.21 μg/mL, a dark-brown material, was separated on a semipreparative reversed-phase HPLC Zorbax SB $C_{18}$ column with 85:15 $CH_3OH$—$H_2O$ (a flow rate of 4 mL/min and the UV detector set at 208 nm).

Turbostatins 1 and 2 were obtained in the following order: Turbostatin 1 (10.1 mg) at 20.5 minutes and turbostatin 2 (11.2 mg) at 25.1 minutes. A 103-mg fraction with $ED_{50}$ 0.56 μg/mL was separated on a semipreparative reversed-phase HPLC Zorbax SB $C_{18}$ column with 85:15 $CH_3OH$—$H_2O$ (a flow rate of 4 mL/min and the UV detector set at 208 nm). The result was that turbostatin 3 and turbostatin 4 were obtained in the following order: turbostatin 3 at 23.7 minutes and turbostatin 4 (8.3 mg) at 28.5 minutes.

All four new compounds were colorless and had very limited solubility in $CH_3OH$, $CH_2Cl_2$, $CH_3CN$, and $H_2O$.

Characterization of the Novel Compounds

Turbostatin 1 (1) 1-O-β-D-glucopyranosyl-2S-hexadecanoylamino-3R-hydroxy-4E-hexadecene: colorless amorphous solid; mp 207-209° C.; $[\alpha]^{23}_D$+10.2° (c 0.10, pyridine); IR (KBr) $v_{max}$ 3393 (OH), 2950, 1630 (C=O), 1537, 1450, 1083, 1032, and 720 $cm^{-1}$; $^1H$- and $^{13}C$-NMR data see Table 1; APCI-MS (positive) m/z 672 $[M+H]^+$, 654, 510, 492, 384, 254; APCI-HRMS (positive) m/z 672.53192 $[M+H]^+$ (calcd for $C_{38}H_{74}NO_8$, 672.54142).

Turbostatin 2 (2) 1-O-β-D-glucopyranosyl-2S-octadecanoylamino-3R-hydroxy-4E-hexadecene: colorless amorphous solid; mp 209-210° C.; $[\alpha]^{23}_D$+10.7° (c 0.10, pyridine); IR (KBr) $v_{max}$ 3394 (OH), 2950, 1631 (C=O), 1538, 1450, 1084, 1030, and 720 $cm^{-1}$, $^1H$- and $^{13}C$-NMR data appear in Table 1; APCI-MS (positive) m/z 700 $[M+H]^+$, 682, 538, 520, 412, 254; APCI-HRMS (positive) m/z 700.57498 $[M+H]^+$ (calcd for $C_{40}H_{78}NO_8$, 700.57272).

Turbostatin 3 (3) 1-O-β-D-galactopyranosyl-2S-hexadecanoylamino-3R-hydroxy-4E-hexadecene: colorless amorphous solid; mp 213-214° C.; $[\alpha]^{23}_D$=6.3° (c 0.10, pyridine); IR (KBr) $v_{max}$ 3395 (OH), 2951, 1633 (C=O), 1537, 1450, 1085, 1031 and 720 $cm^{-1}$; $^1H$- and $^{13}C$-NMR data refer to Table 2; APCI-MS (positive) m/z 672 $[M+H]^+$, 654, 510, 492, 384, 254; APCI-HRMS (positive) m/z 672.53979 $[M+H]^+$ (calcd for $C_{38}H_{74}NO_8$, 672.54142).

Turbostatin 4 (4) 1-O-β-D-galactopyranosyl-2S-octadecanoylamino-3R-hydroxy-4E-hexadecene: colorless amorphous solid; mp 214-215° C.; $[\alpha]^3_D$=6.5° (c 0.10, pyridine); IR (KBr) $v_{max}$ 3394 (OH), 2950, 1632 (C=O), 1538, 1451, 1084, 1030 and 720 $cm^{-1}$; $^1H$- and $^{13}C$-NMR data see Table 2; APCI-MS (positive) m/z 700 $[M+H]^+$, 682, 538, 520, 412, 254; APCI-HRMS (positive) m/z 700.58320 $[M+H]^+$ (calcd for $C_{40}H_{78}NO_8$, 700.57272).

The elucidation of the structure of these newly isolated compounds is a significant step towards permitting the synthesis of the compounds. It is important to be able to synthesize compounds that otherwise can be obtained from nature, due to problems with obtaining sufficient amounts of the starting material, the difficulty of separating useful compounds from the starting material and from non-useful and/or harmful other components, and the challenges of removing impurities. Moreover, the isolation/purification of these compounds may permit one or more of the compounds or their salts to be used in dosages which can be low enough to be tolerated by hosts with minimal adverse effects from impurities.

In Vitro Testing of Activity of Novel Compounds.

Cancer Cell Line Methods. The National Cancer Institute's standard sulforhodamine B assay was used to assess inhibition of human cancer cell growth. The murine P388 lymphocytic leukemia cell line results were obtained using 10% horse serum/Fisher medium with incubation for 24 hours. Serial dilutions of the compounds were added, and after 48 hours, cell growth inhibition ($ED_{50}$) was calculated using a Z1 Coulter particle counter.

Pharmaceutical Compositions and Dosage Forms

Pharmaceutical compositions can be used in the preparation of individual dosage forms. Consequently, pharmaceutical compositions and dosage forms of the invention comprise the active ingredients disclosed herein. The notation of "active ingredient" signifies the compounds of the invention described herein. Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a neoplastic disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

As used herein, a "therapeutically effective amount" is an amount sufficient to either inhibit (partially or totally) formation of a tumor or a hematological malignancy or to reduce its further progression. For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art.

Possible illustrative dosage forms of the invention comprise a compound or mixture of compounds of the invention thereof as an active ingredient in an amount of from about 1 mg to about 2000 mg, more preferably from about 25 mg to about 1000 mg, even more preferably from about 50 mg to about 750 mg, and most preferably from about 100 mg to about 500 mg.

For illustrative purposes, dosage levels of the administered active ingredients may be: intravenous, 0.01 to about 20 mg/kg; intramuscular, 0.1 to about 50 mg/kg; orally, 0.05 to about 100 mg/kg; intranasal instillation, 0.5 to about 100 mg/kg; and aerosol, 0.5 to about 100 mg/kg of host body weight.

Expressed in terms of concentration, an active ingredient may be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v The active ingredients to be employed as antineoplastic agents can be easily prepared in such unit dosage form with the employment of pharmaceutical materials which themselves are available in the art and can be prepared by established procedures. The following preparations are illustrative of the preparation of dosage forms of the present invention, and not as a limitation thereof.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous, bolus injection, intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts of the active ingredients can be used to further adjust the properties of the resulting composition.

The preceding technological disclosure describes illustrative embodiments of these Turbostatin compounds and their proposed use and does not intend to limit the present invention to these precise embodiments. Further, any changes and/or modifications, which may be obvious by one with ordinary skill in the related art, including but not limited to pharmaceutical salt derivatives or non-functional changes of the disclosed chemical (Turbostatin) compounds, are intended to be included within the scope of the invention.

REFERENCES AND NOTES (1) For contribution 544, refer to Bai, R.; Covell, D. G.; Kepler, J. A.; Copeland, T. D.; Nguyen, N.Y.; Pettit, G. R.; Hamel, E. *J. Biol. Chem.*, in preparation.
(2) Halstead, B. W., *Poisonous and Venomous Marine Animals for the World*, Vol. 1, p. 708, U.S. Government Printing Office Washington, D.C., 1965.
(3) (a) Pettit, G. R.; Day, J. F.; Hartwell, J. L.; Wood, H. B. Nature 1970, 227, 962-963. (b) Schwartsmann, G.; Brondani da Rocha, A.; Mattei, J.; Lopes R. M. *Expert Opin. Investig. Drugs* 2003, 12, 1367-1383. (c) Haefner, B. *DDT* 2003, 8, 536-544. (d) Kingston, D. G. I.; Newman, D. J. *Drug Discovery & Dev.* 2002, 15, 304-316. (e) Luesch, H.; Harrigan, G. G.; Goetz, G.; Horgen, F. *D. Curr. Med. Chem.* 2002, 9, 1791-1806.
(4) Pettit, G. R.; Ode, R. H.; Harvey, T. B., III Lloydia 1973, 36, 204-206.
(5) (a) Kono, N.; Yamakawa, H. *Bull. Fisheries Res. Agency* 2002, 19-24. (b) Poulicek, M. *Malacologia* 1982, 22, 235-239.
(6) Murata, K.; Watanabe, S.; Takagi, K. *Mer-Tokyo* 1988, 26, 29-35.
(7) Pettit, G. R.; Houghton, L. E.; Rogers, N. H.; Coomes, R. M.; Berger, D. F.; Reucroft, P. R.; Day, J. F.; Hartwell, J. L.; Wood, H. B. *Experimentia* 1971, 28, 382.
(8) Babu, U. V.; Bhandari, S. P. S.; Garg, H. S. *J. Nat. Prod.* 1997, 60, 732-734.
(9) Kawatake, S.; Nakamura, K.; Inagaki, M.; Higuchi, R. *Chem. Pharm. Bull.* 2002, 50, 1091-1096.
(10) Sitrin, R. D.; Chan, G.; Dingerdissen, J.; Debrosse, C.; Mehta, R.; Roberts, G.; Rottschaefer, S.; Staiger, D.; Valenta, J.; Snader, K. M.; Stedman, R. J.; Hoover, J. R. E. *J. Antibiot.* 1988, 41, 469-480.
(11) Chen, J. H.; Cui, G. Y.; Liu, J. Y.; Tan, R. X. *Phytochemistry* 2003, 64, 903-906.
(12) Bock, K. Pederson, C. In *Advances in Carbohydrate Chemistry and Biochemistry*, Jipson, R. S.; Horfon, D., Eds.; Academic Press: New York, 1983; Vol. 41, pp 27-46.
(13) Kong, L. D.; Abliz, Z.; Zhou, C. X.; Li, L. J.; Cheng, C. H. K.; Tan, R. X. *Phytochemistry* 2001, 58, 645-651.
(14) Chen, X.; Wu, Y.-L.; Chen, D. *Tetrahedron Lett.* 2002, 43, 3529-3532.
(15) Kolter, T.; Sandhoff, K. *Angew. Chem. Int. Ed.* 1999, 38, 1532-1568.
(16) Kang, S. S.; Kim, J. S.; Xu, Y. N.; Kim, Y. H. *J. Nat. Prod.* 1999, 62, 1059-1060.
(17) Sugiyama, S.; Honda, M.; Komoro, T. *Liebigs Ann. Chem.* 1990, 1069-1078.
(18) Sugiyama, S.; Honda, M.; Higuchi, R.; Komoro, T. *Liebigs Ann. Chem.* 1991, 349-356.
(19) Jung, J. H.; Lee, C. O.; Kim, Y. C. Kang, S. S. *J. Nat. Prod.* 1996, 59, 319-322.
(20) Pushkareva, M.; Obeid, L.; Hannun, Y. *Immunol. Today* 1994, 16, 294.
(21) Raines, M. A.; Kolesnick, R. N.; Golde, D. W. *J. Biol. Chem.* 1993, 268, 14572-14575.
(22) Huwiler, A.; Brunner, J.; Hummel, R.; Vervoordeldonk, M.; Stabel, S.; van den Bosch, H.; Pfeilschifter, *J. Proc. Natl. Acad. Sci. USA* 1996, 93, 6959-6963.
(23) Tan, R. X.; Chen, J. H. *Nat. Prod. Rep.* 2003, 20, 509-534.
(24) Plettenburg, O.; Boddmer-Narkevitch, V.; Wong, C. H. *J. Org. Chem.* 2002, 67, 4559.
(25) Morita, M.; Motoki, K.; Akimoto, K.; Natori, T.; Sakai, T.; Sawa, E.; Yamaji, K.; Koezaka, Y.; Kobayashi, E.; Fukushima, H. *J. Med. Chem.* 1995 38, 2176.

(26) Motoki, K.; Kobayashi, E.; Uchida, T.; Fukushima, H.; Koezuka, Y. *Bioorg. Med. Chem. Lett.* 1995, 140, 705.
(27) Monks, A.; Scudiero, D.; Skehan, P.; Shoemaker, R.; Paull, K.; Vistica, D.; Hose, C.; Langley, J.; Cronise, P.; Vaigro-Wolff, A.; et al. *J. Natl. Cancer Inst.* 1991, 83, 757-766.

What is claimed is:

1. An isolated compound having the following structure:

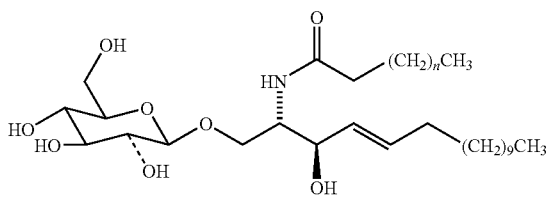

wherein n=13, and salts thereof.

2. An isolated compound having the following structure:

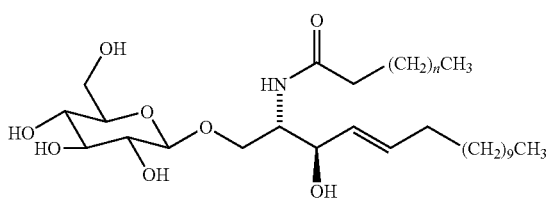

wherein n=15, and salts thereof.

3. An isolated compound having the following structure:

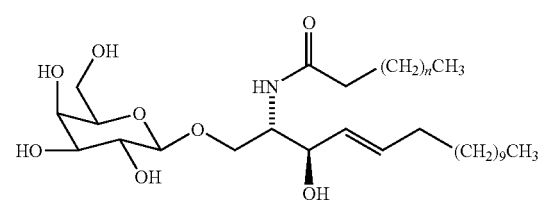

wherein n=13, and salts thereof.

4. An isolated compound having the following structure:

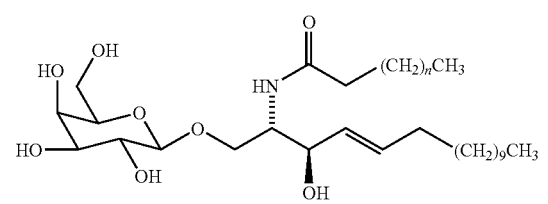

wherein n=15, and salts thereof.

5. A composition comprising the compound of claim 1 and a pharmaceutically acceptable carrier.

6. A composition comprising the compound of claim 2 and a pharmaceutically acceptable carrier.

7. A composition comprising the compound of claim 3 and a pharmaceutically acceptable carrier.

8. A composition comprising the compound of claim 4 and a pharmaceutically acceptable carrier.

9. A method for treating a neoplastic disease in a patient, comprising administering to the said patient an effective amount of the composition of claim 5.

10. A method for treating a neoplastic disease in a patient, comprising administering to the said patient an effective amount of the composition of claim 6.

11. A method for treating a neoplastic disease in a patient, comprising administering to the said patient an effective amount of the composition of claim 7.

12. A method for treating a neoplastic disease in a patient, comprising administering to the said patient an effective amount of the composition of claim 8.

13. A method for the isolation of a compound selected from the group consisting of

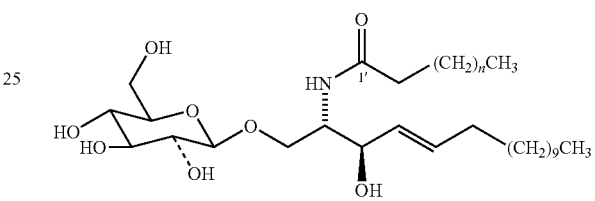

wherein n=13 or 15 or

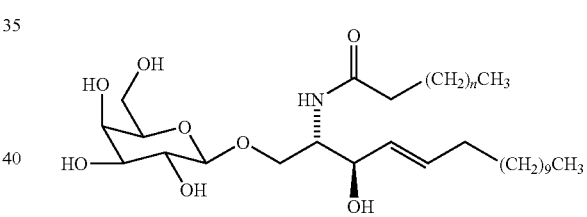

wherein n=13 or 15 comprising the steps of:
  a. forming a 2-propanol extract of *Turbo stenogyrus;*
  b. subjecting the 2-proponal extract to a 9:1→3:2 $CH_3OH$—$H_2O$/Hexane→$CH_2Cl_2$ solvent partition sequence to product a methylene chloride extract;
  c. fractionating the methylene chloride extract via a series of separations involving column gel permeation (Sephadex LH-20), partition chromatography;
  d. subjecting the fractionated extract by reverse-phase HPLC columns on Zorbax SB-C18 in 85:15 $CH_3OH$—$H_2O$;

to obtain the compounds.

* * * * *